(12) United States Patent
Cregger et al.

(10) Patent No.: US 8,481,331 B2
(45) Date of Patent: Jul. 9, 2013

(54) OXIDATIVE DYE COMPOSITION AND INDICATOR

(75) Inventors: Tricia Cregger, Fairlawn, OH (US); Randal W. Eveland, Concord, OH (US); Antoinette Bower, Mentor, OH (US)

(73) Assignee: American Sterilizer Company, Mentor, OH (US)

( * ) Notice: Subject to any disclaimer, the term of this patent is extended or adjusted under 35 U.S.C. 154(b) by 1169 days.

(21) Appl. No.: 11/222,335

(22) Filed: Sep. 8, 2005

(65) Prior Publication Data

US 2007/0054412 A1 Mar. 8, 2007

(51) Int. Cl.
*G01N 21/75* (2006.01)
(52) U.S. Cl.
USPC .................. 436/166; 436/19; 436/38; 422/50
(58) Field of Classification Search
USPC .................. 436/19, 38, 166; 422/56
See application file for complete search history.

(56) References Cited

U.S. PATENT DOCUMENTS

| 3,288,718 A | | 11/1966 | Carumpalos | |
|---|---|---|---|---|
| 4,349,509 A | * | 9/1982 | Yoshikawa et al. | 422/426 |
| 5,264,348 A | * | 11/1993 | Schick et al. | 435/28 |
| 2002/0051733 A1 | | 5/2002 | Antonoplos et al. | |
| 2003/0118478 A1 | | 6/2003 | Hehenberger | |
| 2003/0131786 A1 | * | 7/2003 | Kauzlarich et al. | 117/88 |
| 2003/0194346 A1 | | 10/2003 | Read | |
| 2003/0211618 A1 | * | 11/2003 | Patel | 436/38 |

FOREIGN PATENT DOCUMENTS

| EP | 1 163 913 | 12/2001 |
|---|---|---|
| GB | 2 002 517 | 2/1979 |

OTHER PUBLICATIONS

Sodium Methoxide MSDS (2004) Analytyka.*
Anonymous, "Prehumidifcation, Oxyfume Secondary Sterilization Process and Aeration for Medical Products", Research Disclosure, Mason Publications, Hampshire, Great Britain, vol. 410, No. 66, Jun. 1998, XP007122891.

* cited by examiner

*Primary Examiner* — Krishnan S Menon
*Assistant Examiner* — Rebecca M Fritchman
(74) *Attorney, Agent, or Firm* — Hudak, Shunk & Farine Co. LPA

(57) ABSTRACT

An oxidative dye indicator composition comprising an indicator dye that has been pre-reacted with a reducing agent prior to use in an oxidizing or disinfectant sterilizing system. The pre-reacted dye, when subjected to an oxidizing disinfection or sterilization agent, such as peracetic acid or hydrogen peroxide, under goes a visible color change and thus can serve as a chemical, process, or chemical integrator, indicator. The dyes include various azines, thiazines, and oxazines compounds and the reducing agents include alkali metal alkoxides and alkaline earth metal alkoxide compounds.

17 Claims, No Drawings

OXIDATIVE DYE COMPOSITION AND INDICATOR

FIELD OF THE INVENTION

The present invention relates to an oxidative dye solution, composition, and indicator that detects whether articles such as medical devices have been subjected to an oxidizing disinfection or sterilization process or treatment. More specifically, the present invention relates to the formation of oxidative dye solutions by prereaction of an indicator dye with a reducing agent that is applied as a solution containing a solvent and a binder to a substrate and dried to form an oxidative dye indicator which upon reaction with an oxidizing agent produces a notable color change.

BACKGROUND OF THE INVENTION

Heretofore, there has been a constant need in the fields of disinfection and sterilization to have indicators present during the sterilization or disinfection of medical devices to demonstrate that processed articles have been exposed to the active ingredient of the disinfectant or sterilant. There are several types of indicators used in the field, each providing various levels of assurance to the user that the appropriate processing requirements were met.

The first type of indicator is a process indicator. A process indicator provides an indication to the user that the articles were processed, but not whether or not the appropriate conditions for sterilization or disinfection were achieved during the processing cycle. Commonly, process indicators are colorimetric in nature and appear on the labeling of self-contained biological indicators (SCBI) or on autoclave tape. The color change of this type of indicator is almost instantaneous.

A second type of indicator is a chemical indicator (CI). A chemical indicator is able to detect semi-quantifiable to quantifiable amounts of the active used in the sterilization or disinfection process. The use of a chemical indicator with various articles provides a high level of assurance that the required active concentration was achieved. Chemical indicators are commonly placed with articles to demonstrate that the active ingredient was able to completely penetrate the processed articles. For instance, CIs may be placed within a wrapped pack that is being steam sterilized.

Chemical integrators are yet another type of indicator. Integrators will measure more than one parameter. For instance, an integrator will not only indicate that the appropriate concentration of active was achieved but that the active remained at the concentration for the minimum time required. Another common variable that may be measured by integrators is the temperature of the system.

The final type of indicator is the biological indicator (BI). Biological indicators provide a high degree of assurance that sterilization conditions were met within the processor or processed articles. This type of indicator is meant to represent the worst case for the processing system by providing an extremely high number of highly resistant organisms to that particular process within or on the indicator. Usually spores are the organism of choice for sterilization systems.

Currently, many process and chemical indicators for oxidative high level disinfection systems and sterilization processes, such as liquid peracetic acid (PAA) and hydrogen peroxide ($H_2O_2$), rely on an oxidative bleaching-type reaction resulting in a gradual decrease in the color intensity with exposure time and/or active concentration. Indicators that do not rely on an oxidative bleaching reaction may change color with PAA or $H_2O_2$ in the presence of either a halogen source or a transition metal salt.

A commercial chemical indicator (i.e. STERIS System 1 Chemical Indicator) contains a dye that exhibits a vivid purple color before exposure to liquid peracetic acid, and after exposure to appropriate levels of peracetic acid, the indicator is a light pale gray color. The color change result is due the indicator dye being oxidatively bleached by the peracetic acid during the processing cycle. Another commercial indicator is magenta and upon exposure to the oxidative capacity of peracetic acid changes to peach. The peach color results from an underlying dye that is not susceptible to oxidation.

The 3M Comply 1249 Liquid Peracetic Acid Chemical Indicator requires a halide salt (alkaline earth metal halide or alkali metal halide salt) to obtain the color change in the dye when exposed to peracetic acid vapors. The vapor from the peracetic acid penetrates through the vapor permeable backing of the chemical indicator blister pack and oxidizes the halide salt to release the halogen. The halogen then reacts with the indicator dye (in the sodium salt form) to change the color.

Other chemical indicators for vaporous hydrogen peroxide sterilization processes rely on the oxidative nature of the $H_2O_2$ either directly or indirectly. For instance, a chemical indicator for vaporous hydrogen peroxide systems can contain metal salt in addition to at least one indicator dye. The $H_2O_2$ reacts with the metal salt which in turn reacts with dye to get a distinct color change.

While the above indicators and methods are generally effective, they may be complex to manufacture and expensive to use. They also rely on interactions with a halide salt or by other direct means to achieve a desired color change.

SUMMARY OF THE INVENTION

The present invention relates to a prereacted dye formed by the reaction of an indicator dye with a reducing agent, that provides a notable or distinct color change to aide in the interpretation of a process indicator, a chemical indicator, or a chemical integrator indicator. The prereacted dye desirably is to be blended with a binder and a solvent and the entire solution applied to a suitable substrate such as paper, polymer, or polymer composite, glass silicon, etc., to form an oxidative dye indicator upon drying.

In general, an oxidative dye composition comprises an indicator dye pre- reacted with a reducing agent, said reducing agent comprising at least one alkali metal alkoxide, alkaline earth metal alkoxide, borane, borohydride, silicone compound, Group I or Group II metal hydride, alkali benzophenone, or alkyl sodium or alkyl lithium, or combinations thereof; and said pre-reacted dye upon reaction with an oxidizing agent being capable of producing a color change.

The following definitions serve to illustrate the present invention.

Indicator Dye generally means a dye that is reacted with a Reducing Agent to form a Prereacted Dye.

Reducing Agent generally means a compound which reacts with the Indicator Dye to form said Preacted Dye.

Prereacted Dye generally means a compound formed by the reaction of said Indicator Dye with said Reducing Agent.

Solvent generally means a substance capable of dissolving said Prereacted Dye to form a mixture.

Binder generally means a film forming ingredient such as a polymer, polymer precursor, or thickening agent.

Oxidative Dye Solution generally means a mixture of a Prereacted Dye, said Solvent, and said Binder.

Oxidative Dye Composition generally means a dried Oxidative Dye Solution.

Substrate generally means a material to which the Oxidative Dye Solution is applied which forms an Oxidative Dye Indicator either in a wet or dry state.

DETAILED DESCRIPTION OF THE INVENTION

The prereacted dye of the present invention is made by reacting an indicator dye with a reducing agent. The indicator dye comprises various one or more organic moiety containing aromatic compounds having at least one nitrogen atom in the ring and at least one or more remaining atoms within the ring that are either another nitrogen atom, or an oxygen atom, or a sulfur atom, or combinations thereof. Such dyes can have the following basic structure.

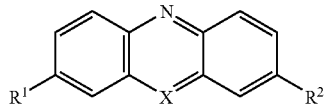

where X=N, e.g. an azine, X=O, e.g. oxazine; X=S, e.g. thiazine; and the like. $R^1$ and $R^2$, independently, can be any organic moiety, containing from 1 to about 30 carbons or in combination with other elements such as nitrogen, oxygen, chlorine, or an alkali metal, etc., such as methyl, ethyl, hydroxyl, alkyl amines, and sodium salts. The chemical formulations of such dyes including those set forth hereinbelow are well known to the literature and to the art. For example, methylene blue has the formulation

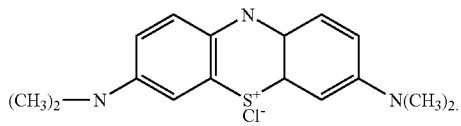

Examples of suitable thiazines include methylene blue, toluidine blue O, methylene violet, methylene green, thionin, azure A, azure A eosinate, azure B, azure B eosinate, azure B tetrafluoroborate, azure C, azure II, or azure II eosinate, or combinations thereof, with methylene blue being preferred.

Examples of suitable oxazines include basic blue 3, resorufin, celestine blue, brilliant cresyl blue ALD, or resazurin, or combinations thereof, with resazurin being preferred.

Examples of suitable azine compounds include mauveine Janus green, and Nigrosine (aniline black), or combinations thereof with Janus green being preferred.

The reducing agent is a compound which can optionally change the color of the indicator dye when reacted therewith, but upon formation of the oxidative dye solution or composition will effect a color change when reacted with an oxidizing agent or an oxidizing-bleaching agent. Effective reducing agents include various alkali metal alkoxide compounds or the alkaline earth metal alkoxide compounds, other non-metallic reducing agents (such as boranes or borohydrides or silicone compounds), Group I or Group II metal hydrides, alkali benzophenone, alkyl sodium or alkyl lithium compounds, or combinations thereof. The alkoxide group has from 1 to about 4 carbon atoms. Examples of such specific reducing agents include, but are not limited to, sodium methoxide, sodium ethoxide, sodium propoxide, sodium butoxide, potassium methoxide, potassium ethoxide, potassium propoxide, potassium butoxide, calcium methoxide, calcium ethoxide, calcium propoxide, calcium butoxide, magnesium methoxide, magnesium ethoxide, magnesium propoxide, and magnesium butoxide. The boranes or borohydrides generally have the formula $B_nH_{n+4}$ or $B_nH_{n+6}$ where n=1 to about 10 and include diborane, tetraborane, pentaborane, or combinations thereof. Silicone compounds include various organosiloxane polymers wherein the viscosity can range from about 1 to about 1 million centistokes. Group I and Group II metal hydrides include sodium hydride, potassium hydride, magnesium hydride, calcium hydride, and the like. The various alkyl sodium or alkyl lithium compounds contain from 1 to about 20 carbon atoms and desirably from about 1 to about 4 carbon atoms. Preferred reducing agents include alkali and alkaline earth alkoxides such as sodium methoxide, sodium ethoxide, potassium methoxide, and the like.

The prereacted dye can be made by generally reacting from about 0.002 to about 0.060 moles and desirably from about 0.010 moles to about 0.030 moles of the indicator dye with one mole of the reducing agent generally at a temperature of about 10° C. to about 40° C. and desirably from about 15° C. to about 25° C. The indicator dye is reacted with the reducing agents for a period from 1 minute to about 24 hours and desirably from about 5 minutes to about 30 minutes.

In order that the prereacted dye can be readily applied to a substrate, it is generally in the form of an oxidative dye solution and thus contains one or more solvents as well as one or more binders so that it is adheres to the substrate. The solvents can be aqueous or organic that dissolve and/or emulsify the oxidative dye composition and are volatile so that following application to the substrate, the solvent evaporates leaving the oxidative dye composition bound to the substrate by the binder. Numerous polar solvents exist with one type being various alcohols having from 1 to about 6 carbon atoms such as methyl alcohol, ethyl alcohol, isopropyl alcohol, tertiary butyl alcohol, methoxyethanol and others known to those skilled in the art, with methoxyethanol being desired. Other polar solvents include various ketones having a total of from about 2 to about 8 carbon atoms such as methyl ethyl ketone, diethyl ketone, 2-hexanone, 3-hexanone, and the like. Another class of polar solvents are the various acetates having a total of from about 3 to about 1 2 carbon atoms such as N-butyl acetate, and the like. Examples of effective non-polar solvents include aromatic hydrocarbons having a total of from 6 to about 20 carbon atoms such as benzene, toluene, xylene, σ, m, ρ-napthalene, and others known to those skilled in the art.

The amount of the various one or more solvents is generally from about 1 to about 10,000 parts and desirably from about 25 or about 50 to about 100 or about 1 50 parts by weight per 1 part by weight of the total weight of the prereacted dye.

Another important component of the oxidative dye solution is a binder which upon evaporation of the solvent will bind the oxidative chemical indicator to the substrate. Suitable binders can be cellulose or derivatives thereof such as cellulose acetate, cellulose acetate butyrate, ethyl cellulose, hydroxypropyl methylcellulose, methyl cellulose, hydroxypropyl cellulose, hydroxyethyl cellulose, nitrose cellulose, and the like with ethyl cellulose being preferred for a liquid-based sterilization and high level disinfection systems because it is water insoluble. Other suitable binders include polymers such as polyvinyl alcohols, polystyrene, polyethylene, and polyacrylates, or a natural occurring resin such as shellac.

The amount of the binder is generally an amount to effectively bind the prereacted dye solution to the substrate and can vary from about 0.001 part to about 0.5 parts by weight per every 1 part by weight of the solvent.

The oxidative dye solution is generally applied to a substrate which is subsequently applied to an oxidizing medium, environment, and the like. The indicator dye thus resides on the substrate generally in the form of a layer or a coating. Suitable substrates include paper or other forms of cellulose such as paper mats, thin sheets of paper board, filtration-type paper, and the like. Other substrates include woven or non-woven fibers such as fabrics made from natural materials as for example, cotton, wool, and the like, or synthetic fibers such as polyester, nylon, polypropylene, polyethylene, and other polymers or polymer blends, and the like. Non-woven fibers include wool felt or cotton felt, and the like. The size and thickness of the substrate can vary depending upon the desired end use as known to the literature and to the art.

The application of the oxidative dye solution to the substrate can occur according to any of several methods with the following serving to exemplify but not to limit the same.

In one embodiment, a dye and a binder are dissolved in a suitable solvent system, excluding the reducing agent. The reducing agent is added after all other components have been dissolved. After a sufficient time is allowed (5 minutes to about 30 minutes or longer) for the reducing agent to react with the indicator dye, the oxidative dye solution is applied to the substrates by dipping, inoculating, spraying, and the like or printed using silk screening or flexographic methods and dried to form the oxidative dye indicator.

In another embodiment, an indicator dye and binder are dissolved in a solvent system (solution 1). A second indicator dye and a dissolved binder in the same solvent system as in solution 1, is mixed and a reducing agent added thereto (solution 2). The substrate is then dipped (inoculated or sprayed) in the first oxidative dye solution and dried. The dried substrates are then exposed to the second oxidative dye solution by dipping, inoculating, or spraying and dried. An advantage to this method is that the reaction rate between the indicator dye and the reducing agent is also reduced.

Yet another embodiment is wherein an indicator dye and binder are dissolved in a solvent system (solution 1). A second solution is made containing a binder such as ethyl cellulose and solvents, to which a reducing agent can be added (solution 2). The substrates are then dipped into solution 1 and dried. Then those same substrates are dipped into solution 2 and dried. An advantage to this method is that the reaction rate between the indicator dye and the reducing agent is reduced.

An improvement of the present invention to the art is that the oxidative dye indicator be it a chemical indicator, process indicator, or a chemical integrator indicator, gives improved calorimetric response when subjected to a disinfectant or sterilization system or process utilizing various oxidizing agents as set forth hereinabove. In other words, generally notable color changes with respect to the indicator are visually apparent. One way of determining the color change is according to a chromaticity diagram called CIE 1976 L*a*b. As known to the literature and to the art, this system describes color along three axes as follows:

L-values are indicative of the luminosity (dark/light aspect) of the color
a-values describe the green to red gamut
b-values describe the blue to yellow gamut An important advantage of the present invention is that a person is able to immediately determine that the oxidative dye indicator actually contains a prereacted dye therein. That is, the oxidative dye indicator initially has a "color 1". Upon contact with a disinfectant or sterilization solution, "color 1" immediately changes to a different "color 2". Change to a "color 3" is both time dependent and concentration dependent with respect to contact of the disinfectant or sterilization agent. With respect to a thiazine dye prereacted with sodium methoxide, "color 1" is purple, "color 2" is blue, and "color 3" after a set time and at 100% concentration is green. Thus, the initial color change from "color 1" to "color 2" allows an end user to visually determine if the prereacted indicator dye has been exposed to the oxidative chemistry of the disinfectant or a sterilant even though the disinfectant or sterilization cycle is later aborted. As a result, the oxidative dye indicator of the present invention serves as a process indicator in addition to a chemical indicator or integrator.

It has been found that the color changes from "color 2" to "color 3" generally has a minimum "a" value change of at least about 12 and desirably at least about 25, and a minimum color change of the "b" value color change of at least about 35 and desirably at least about 50.

The oxidative dye indicators of the present invention are desirably utilized with regard to systems and processes for oxidative high level disinfection and sterilization processes. Suitable disinfection and sterilization agents include various aldehydes, various peroxygens, and various phenols.

Examples of aldehydes include formaldehyde, glutaraldehyde, ortho-phthaldehyde, or formaldehyde-releasing agents such as hexamethylenetetramine, triazines, imidazoles, or hydantoins, and combinations thereof.

A preferred class of disinfection and sterilization agents are various peroxygens which include peracids such as peracetic acid, perchromic acid, persulfuric acid, perbenzoic acid. Other oxidizing agents include, organic or inorganic peroxides such as hydrogen peroxide, percarbonic acid, permanganate, perlauric acid, perglutaric acid, or magnesium peroxyphthalate, and combinations thereof. Preferred compounds include peracetic acid and hydrogen peroxide.

The phenols include substituted phenols such as cresols and bisphenols. Examples include alkyl and dialkyl phenols; dihydric phenols such as catechol, resorcinol, and hydroquinone; alkyl dihydroxybenzenes; halogen substituted phenols such as chlorophenols, alkyl and/or amomatic substituted chlorophenols; nitrophenols, dinitrophenols, trinitrophenols, and alkyl or aromatic substituted nitrophenols; aminophenols; aromatic, alkyl aromatic, and aromatic alkyl substituted phenols; hydroxybenzoic acids; bisphenols, bis(hydroxyphenyl) alkanes, and hydroxyquinolines such as 8-hydroxyquinoline, and combinations thereof. Desired phenolic compounds include o-phenylphenol (OPP), p-t-amylphenol (PTAP), o-benzyl- p-chlorophenol (OBPCP), p-chloro-m-xylenol (PCMX), 5-chloro-2-(2,4-dichlorophenoxy)phenol (Triclosan), and combinations thereof.

Depending upon the type of indicator dye, the rate of which the indicator dye goes to final color will vary. However, this color rate of change can be increased by increasing the ratio of the dye concentration to the binder concentration. An alternative method for controlling the rate of reaction is the addition of an inhibitor or retarding agent to the active ingredient. For PAA, an effective inhibitor is sodium thiosulfate.

The oxidative dye indicators of the present invention can be used to monitor the oxidative disinfection and/or sterilization systems and processes for the treatment of various articles. Such articles include, medical devices including surgical instruments, telescopes, cameras, and the like; medical aid devices such as syringes, tubing, catheters, and the like; medical lumen devices such as scopes (endoscopes, bronchoscopes, urethroscopes, sigmoidoscopes, etc.), and the like; various implantables; various medical mortuary items; various dental devices; various tattooing/piercing equipment; various operating theater equipment/surfaces; and various veterinary equipment. Other articles include manufactured devices such as pharmaceutical items.

The present invention will be better understood by reference to the following examples which serve to illustrate but not to limit the present invention.

EXAMPLES

The following is the formulation which was utilized to prepare the indicators set forth in Example 1:

Formulation for 32.5 mL solution: ethyl cellulose-0.375g (binder); methylene blue-0.0187g (indicator dye); ethanol-5 mL (solvent); toluene-20 mL (solvent); sodiumjnethoxide titrant (0.5 M)-7.5 mL (reducing agent).

The ethyl cellulose, methylene blue, ethanol, and toluene were mixed together until both the binder and dye were fully dissolved. Then the sodium methoxide titrant was added to the mixture and the solution was further mixed for 20 minutes. Then strips were dipped into the solution and allowed to air dry. Once dry the strips were then exposed to various concentrations of sterilants as set forth in the table.

The L*a*b readings of the indicator color after exposure to various peracetic acid concentrations for 10 minutes are exemplified below. The readings below are characteristic for indicator articles made with methylene blue as the indicator dye.

| peracetic acid (parts per million) | L* | a** | b*** |
|---|---|---|---|
| CTRL | 52.71 | 3.65 | −16.32 |
| 0 | 62.74 | 1.79 | −13.73 |
| 521 | 69.69 | −1.66 | −12.49 |
| 707 | 70.18 | −1.55 | −4.09 |
| 906 | 70.73 | −2.24 | −6.34 |
| 1036 | 77.66 | −2.12 | 4.02 |
| 1109 | 75.87 | −1.69 | 5.33 |
| 1459 | 75.87 | −3.75 | 6.60 |
| 1586 | 73.92 | −3.70 | 6.58 |
| 1937 | 75.26 | −3.72 | 6.05 |

*L: 0-100 (black:white)
**a: −values have a green hue; +values have a red hue
***b: −values have a blue hue; +values have a yellow hue While in accordance with the Patent Statutes, the best mode and preferred embodiments have been set forth, the scope of the invention is not limited thereto, but rather by the scope of the attached claims.

What is claimed is:

1. A color indicator composition, comprising:
a first composition comprising an indicator dye dissolved in a solvent;
a second composition comprising a reducing agent, said reducing agent adapted to react with said indicator dye and form a reduced indicator dye, said reducing agent comprising sodium methoxide, sodium ethoxide, sodium propoxide, sodium butoxide, potassium methoxide, potassium etlaoxide, potassium propoxide, potassium butoxide, calcium methoxide, calcium etlaoxide, calcium propoxide, calcium butoxide, magnesium methoxide, magnesium ethoxide, magnesium propoxide, magnesium butoxide, or an organosiloxane polymer having a viscosity of from 1 to about 1 million centistokes, or any combination thereof; and
said reduced form of said indicator dye adapted to visibly change color upon exposure to hydrogen peroxide, peracetic acid, or ethylene oxide.

2. A color indicator device comprising:
a reduced indicator dye composition derived from a reaction of an indicator dye with a reducing agent, wherein said reducing agent comprising sodium methoxide, sodium ethoxide, sodium propoxide, sodium butoxide, potassium methoxide, potassium ethoxide, potassium propoxide, potassium butoxide, calcium methoxide, calcium ethoxide, calcium propoxide, calcium butoxide, magnesium methoxide, magnesium ethoxide, magnesium propoxide, magnesium butoxide, or an organosiloxane polymer having a viscosity of from 1 to about 1 million centistokes, or any combination thereof;
said reduced indicator dye disposed on a substrate; and
said reduced indicator dye adapted to visibly change color upon exposure to hydrogen peroxide, peracetic acid, or ethylene oxide.

3. A process for forming an indicator device, comprising;
dissolving an indicator dye in a solvent;
separately providing a reducing agent, said reducing agent comprising sodium methoxide, sodium ethoxide, sodium propoxide, sodium butoxide, potassium methoxide, potassium ethoxide, potassium propoxide, potassium butoxide, calcium methoxide, calcium ethoxide, calcium propoxide, calcium butoxide, magnesium methoxide, magnesium ethoxide, magnesium propoxide, magnesium butoxide, or an organosiloxane polymer having a viscosity of from 1 to about 1 million centistokes, or any combination thereof;
reacting said reducing agent with said indicator dye composition and forming a reduced indicator dye; and
applying said reduced indicator dye to a substrate to form said indicator device.

4. The composition according to claim 1, wherein said indicator dye is a thiazine dye or a derivative thereof, an oxazine dye or a derivative thereof, or an azine dye or a derivative thereof, or combinations thereof.

5. The composition according to claim 4, wherein said thiazine dye comprises methylene blue, toluidine blue O, methylene violet, methylene green, thionin, azure A, azure A eosinate, azure B, azure B eosinate, azure B tetrailuoroborate, azure C, azure II, azure II eosinate, or combinations thereof; wherein said oxazine dye comprises basic blue 3, resortifin, celestine blue, brilliant cresyl blue ALD, resazurin, or combinations thereof; and wherein said azine dye comprises mauveine, Janus green, Nigrosine (aniline black); or combinations thereof.

6. The composition according to claim 5, wherein said reducing agent comprises sodium methoxide, sodium ethoxide, potassium methoxide, or combinations thereof, and
wherein said dye comprises methylene blue, resazurin, or Janus green, or combinations thereof.

7. An indicator composition for use in monitoring exposure to an oxidizing disinfectant, or a sterilizing process or a treatment that utilizes hydrogen peroxide, peracetic acid, or ethylene oxide, comprising; a solvent, a binder, and the reduced form of the indicator dye of claim 1, wherein said solvent comprises a ketone having a total of from 2 to about 8 carbon atoms, an acetate having a total of from about 3 to about 12 carbon atoms, an aromatic hydrocarbon having a total of from 6 to about 20 carbon atoms, an alcohol having from 1 to about 6 carbon atoms, or combinations thereof, and wherein said binder comprises cellulose acetate, cellulose acetate butyrate, ethyl cellulose, hydroxypropyl methylcellulose, methyl cellulose, hydroxypropyl cellulose, hydroxyethyl cellulose, or nitrose cellulose, or combinations thereof; a polymer comprising polyvinyl alcohol, polystyrene, polyethylene, or polyacrylate, or combinations thereof; or a natural occurring resin; or combinations thereof.

8. The indicator device according to claim 2, further compriSing a binder capable of binding the reduced form of the indicator dye to the substrate.

9. The indicator device according to claim 2, wherein the indicator dye comprises a thiazine or a derivative thereof, an oxazine or a derivative thereof, or an azine or a derivative thereof, or combinat ons thereof.

10. The indicator device according to claim 9, wherein said thiazine dye comprises methylene blue, toluidine blue O methylene violet, methylene green, thionin, azure A, azure A eosinate, azure B, azure B eosinate, azure B tetrafluoroborate, azure C, azure II, azure II eosinate, or combinations thereof; wherein said oxazine dye comprises basic blue 3, resorufin, celestine blue, brilliant cresyl blue ALD, resazurin, or combinations thereof; or wherein said azine dye comprises mauveine, Janus green, Nigrosine (aniline black), or combinations thereof; and wherein said reducing agent comprises sodium methoxide, sodium ethoxide, potassium methoxide, or combinations thereof.

11. The process according to claim 3 wherein said indicator dye comprises a thiazine or a derivative thereof; an oxazine or a derivative thereof; an azine or a derivative thereof; or combinations thereof.

12. The process according to claim 11, further comprising:
adding a binder to said solvent, wherein said binder comprises cellulose acetate, cellulose acetate butyrate, ethyl cellulose, hydroxypropyl methylcellulose, methyl cellulose, hydroxypropyl cellulose, hydroxyethyl cellulose, nitroso cellulose, or combinations thereof; a polymer comprising polyvinyl alcohol, polystyrene, polyethylene, polyacrylate, or combinations thereof; or a natural occurring resin; or combinations thereof.

13. The process according to claim 11, wherein said substrate comprises paper, cellulose or a derivative thereof, woven or nonwoven fibers, synthetic fibers, or combinations thereof.

14. The process according to claim 13, wherein said thiazine dye comprises methylene blue, toluidine blue O methylene violet, methylene green, thionin, azure A, azure A eosinate, azure B, azure B eosinate, azure B tetrafluoroborate, azure C, azure II, azure II eosinate, or combinations thereof; wherein said oxazine dye comprises basic blue 3, resorufin, celestine blue, brilliant cresyl blue ALD, resazurin, or combinations thereof; or wherein said azine dye comprises mauveine, Janus green, Nigrosine (aniline black), or combinations thereof; and wherein said reducing agent comprises sodium methoxide, sodium ethoxlde, potassium methoxide, or combinations thereof.

15. A process for forming an indicator composition for use in monitoring exposure to an oxidizing disinfectant or a sterilizing process or a treatment that utilizes hydrogen peroxide, peracetic acid, or ethylene oxide, comprising the steps of:

providing an indicator dye comprising a triazine dye, an oxazine dye, an azine dye, or combinations thereof;

separately providing a reducing agent comprising an alkali metal alkoxide or an alkali earth metal alkoxide reacting said reducing agent with said indicator dye to produce a reduced form of the indicator dye; and said reduced indicator dye capable of producing a distinct color change that is visually apparent upon exposure to the hydrogen peroxide, peracetic acid, or ethylene oxide.

16. The indicator device of claim 10, wherein said binder comprises cellulose acetate, cellulose acetate butyrate, ethyl cellulose, hydroxypropyl methylcellulose, methyl cellulose, hydroxypropyl cellulose, hydroxyethyl cellulose, or nitroso cellulose, or combination thereof; a polymer comprising polyvinyl alcohol, polystyrene, polyethylene, or polyacrylate, or combinations thereof; a natural occurring resin; or combinations thereof.

17. The process according to claim 14, wherein said binder comprises cellulose acetate, cellulose acetate butyrate, ethyl cellulose, hydroxypropyl methylcellulose, methyl cellulose, hydroxypropyl cellulose, hydroxyethyl cellulose, nitrose cellulose, or combinations thereof; a polymer comprising polyvinyl alcohol, polystyrene, polyethylene, polyacrylate, or combinations thereof; a natural occurring resin; or combinations thereof.

* * * * *

UNITED STATES PATENT AND TRADEMARK OFFICE
CERTIFICATE OF CORRECTION

PATENT NO. : 8,481,331 B2  
APPLICATION NO. : 11/222335  
DATED : July 9, 2013  
INVENTOR(S) : Tricia Cregger, Randal W. Eveland and Antoinette Bower Page 1 of 1

It is certified that error appears in the above-identified patent and that said Letters Patent is hereby corrected as shown below:

In the Claims:

Claim 1, column 7, lines 61 and 62: replace "etlaoxide" with "ethoxide"

Claim 4, column 8, line 45: replace "resortifin" with "resorufin"

Claim 8, column 9, lines 5-6: replace "compriSing" with "comprising"

Claim 9, column 9, line 11: replace "combinat ons" with "combinations"

Claim 12, column 9, line 34: replace "nitroso" with "nitrose"

Claim 16, column 10, line 30: replace "nitroso" with "nitrose"

Claim 16, column 10, line 31: replace "combination" with "combinations"

Signed and Sealed this
Seventeenth Day of September, 2013

Teresa Stanek Rea
*Deputy Director of the United States Patent and Trademark Office*